(12) United States Patent
Mueller et al.

(10) Patent No.: US 7,494,797 B2
(45) Date of Patent: Feb. 24, 2009

(54) RECOMBINANT TERMINAL DEOXYNUCLEOTIDYL TRANSFERASE WITH IMPROVED FUNCTIONALITY

(75) Inventors: Rainer Mueller, Penzberg (DE); Markus Pajatsch, Munich (DE); Ingo Curdt, Munich (DE); Harald Sobek, Penzberg (DE); Manfred Schmidt, Penzberg (DE); Bernhard Suppmann, Weilheim (DE); Kirsten Sonn, Penzberg (DE); Bernd Schneidinger, Hohenschaeftlarn/Neufahrn (DE)

(73) Assignee: Roche Diagnostics Operations, Inc., Indianapolis, IN (US)

( * ) Notice: Subject to any disclaimer, the term of this patent is extended or adjusted under 35 U.S.C. 154(b) by 283 days.

(21) Appl. No.: 10/406,136

(22) Filed: Apr. 3, 2003

(65) Prior Publication Data

US 2004/0043396 A1    Mar. 4, 2004

(30) Foreign Application Priority Data

Apr. 5, 2002    (DE) ................. 102 15 035

(51) Int. Cl.
*C12N 9/12* (2006.01)
*C12N 9/00* (2006.01)
*C07K 1/00* (2006.01)
(52) U.S. Cl. ................. 435/194; 530/350; 435/183
(58) Field of Classification Search ................. 435/194
See application file for complete search history.

(56) References Cited

U.S. PATENT DOCUMENTS 5,037,756 A    8/1991    Bollum et al. ........... 435/252.3

OTHER PUBLICATIONS

Ngo et al. in The Protein Folding Problem and Tertiary Structure Prediction, 1994, Merz et al. (ed.), Birkhauser, Boston, MA, pp. 433 and 492-495.*
Boule. Jean-Baptiste et al., "High-Level Expression of Murine Terminal Deoxynucleotidyl Transferase in *Escherichia coli* Grown at Low Temperature and Overexpressing argU tRNA," Molecular Biotechnology, vol. 10, 1998, pp. 199-208.
Brinkmann, Ulrich et al., "High-level expression of recombinant genes in *Escherichia coli* is dependent on the availability of the dnaY gene product," Gene, 85 (1989) 109-114.
Chang, Lucy M. S. et al., "Expression and Processing of Recombinant Human Terminal Transferase in Baculovirus System," The Journal of Biological Chemistry, vol. 263, No. 25, pp. 12509-12513, Sep. 5, 1998.
Chang, Lucy M. S. et al., "Molecular Biology of Terminal Transferase," CRC Clinical Reviews in Biochemistry, vol. 21, Issue 1, pp. 27-52, 1986.
Chang, Lucy M. S. et al., "Proteolytic Degradation of Calf Thymus Terminal Deoxynucleotidyl Transferase," The Journabf Biological Chemistry, vol. 257, No. 10, pp. 5700-5706, May 25, 1982.
Deibel, Martin R. et al., "Purification of a High Molecular Weight Human Terminal Deoxynucleotidyl Transferase," The Journal of Biological Chemistry, vol. 254, No. 17, pp. 8634-8640, Sep. 10, 1979.
Garcia, George M. et al., "The *E. coli* dnaY Gene Encodes an Arginine Transfer RNA," Cell, vol. 45, 453-459, May 9, 1986.
Hanahan, Douglas, "Studies on Transformation of *Escherichia coli* with Plasmids," J. Mol. Biol. (1983) 166, 557-580.
Koiwai, Osamu et al., "Isolation and characterization of bovine and mouse terminal deoxynucleotidyl transferase cDNAs expressible in mammalian cells," Nucleic Acids Research, vol. 14, No. 14, 1986, pp. 5777-5792.
Laemmli, U.K., "Cleavage of Structural Proteins during the Assembly of the Head of Bacteriophage T4," Nature, vol. 227, Aug. 15, 1970, pp. 680-685.
Peterson, Ronald C. et al., "Expression of Human Terminal Deoxynucleotidyl Transferase in *Escherichia coli*," The Journal of Biological Chemistry, vol. 260, No. 19, pp. 10495-10502, Sep. 5, 1985.
Yang, Baoli et al., "T-cell specific avian TdT: characterization of the cDNA and recombinant enzyme," Nucleic Acids Research, 1995, vol. 23, No. 11, 2041-2048.
Yanisch-Perron, Celeste et al., "Improved M13 phage cloning vectors and host strains: nucleotide sequences of the M13mp18 and pUC19 vectors," Gene, 33 (1985) 103-119.

* cited by examiner

*Primary Examiner*—Richard G Hutson
(74) *Attorney, Agent, or Firm*—Barnes & Thornburg LLP

(57) ABSTRACT

Truncated terminal deoxynucleotidyl transferase (TdT) derivative from calf thymus, characterized in that the derivative in comparison to the native TdT is N-terminally truncated by up to 161 amino acids and has a 20- to 30-fold higher enzyme activity in solutions containing $Co^{2+}$ ions, and its recombinant production and use.

11 Claims, 2 Drawing Sheets

Figure 2

LS  V    1    2    3    4    LS  V

RECOMBINANT TERMINAL DEOXYNUCLEOTIDYL TRANSFERASE WITH IMPROVED FUNCTIONALITY

Figure 1:
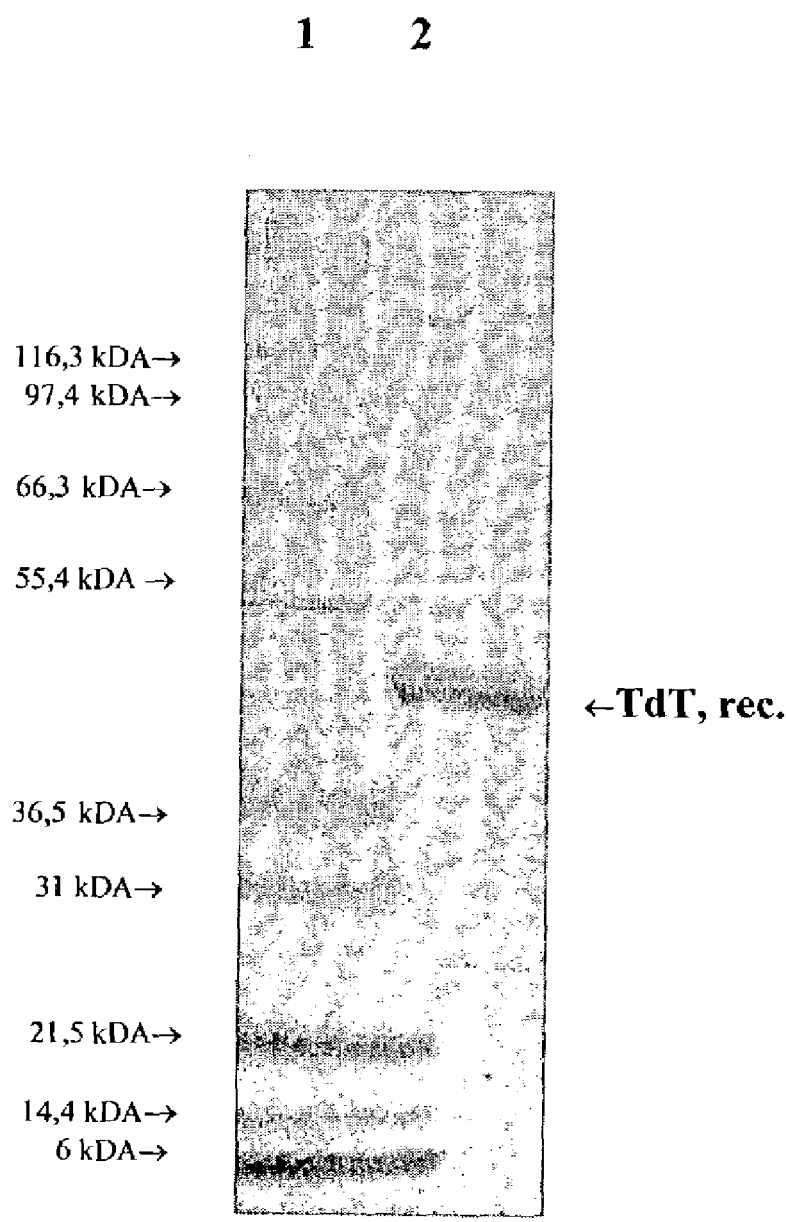

The invention concerns a recombinant N-terminally truncated terminal deoxynucleotidyl transferase (TdT) from calf thymus which, under certain conditions, has an at least 20-fold increased activity compared to the fill-length TdT, as well as the production and use thereof.

Terminal deoxynucleotidyl transferase (TdT) is a highly conserved enzyme from vertebrates that catalyses the attachment of 5' triphosphates to the 3' hydroxyl group of single- or double-stranded DNA. Hence the enzyme acts as a template-independent polymerase (Koiwai et al. (1986), Nucleic Acid Research 14 (14), 5777-5792). In vivo the TdT is responsible for the high diversity of immunoglobulins and T-cell receptors. In addition to the naturally occurring nucleoside triphosphates, TdT usually accepts radioactively labelled triphosphates as well as non-radioactively labelled triphosphates e.g. triphosphates labelled with digoxigenin or biotin. The acceptance of labelled triphosphates also makes the TdT interesting for laboratory and industrial applications (e.g. oligotailing, in situ cell death detection in apoptosis test).

The full length TdT (molecular weight ca. 58000 Da/520 amino acids) is subject in vivo to a stepwise proteolytic degradation to smaller fragments which are, however, still enzymatically active (Chang et al. (1982), *J. Biol. Chem.* 257(10): 5700-5706). Starting at the N-terminus, this proteolytic processing generates peptides of 56 kDa, 44 kDa and 42 kDa molecular weight from the 58 kDa TdT which all still have the active centre. Furthermore it is known that the 42 kDa peptide is degraded into an active TdT fragment having a molecular weight of 32 kDa which is in turn composed of 2 peptides, the α peptide of 8 kDa and the β peptide of 26 kDa. This 32 kDa fragment is also the predominant form when isolated from the calf thymus (Chang and Bollum (1986), *CRC Crit. Rev. Biochem.* 21(1):27-52).

The isolation of TdT from calf thymus has been known for a long time (Deibel and Coleman (1979) *J. Biol. Chem.* 254 (17): 8634-8640). Moreover the method described by Deibel and Coleman is economical on a large scale since calf thymus is a cheap raw material. However, a disadvantage of this method is that, due to the proteolytic activation mentioned above, it is not possible to purify TdT in a homogeneous, pure-band form nor is it possible to separate the active TdT fragments from inactive TdT fragments. Moreover the isolation of substances from bovine raw materials should nowadays be avoided as far as possible due to the problems associated with BSE.

The expression of the human full length TdT in *E. coli* is described in Peterson et al. (1985, *J. Biol. Chem.* 260(19): 10495-502) and in U.S. Pat. No. 5,037,756 (Bollum et al.). The expressed protein was detected in a crude extract of *E. coli* using an antibody to TdT (from the rabbit) and was purified as a full length product by immuno-affinity chromatography. However, the yields of TdT in this method are probably rather small; at least no yields and function tests are described.

In 1988 Chang et al (*J. Biol. Chem.* 263(25): 12509-12513) describe the expression of full length TdT from humans in a baculovirus system. In this case the yields are about 10% of the total protein content; the enzyme exhibits immunological and enzymatic activity. A disadvantage of this method is the relatively low yields that often occur with heterologous protein expression in the baculovirus system compared to prokaryotic expression systems and the higher production costs of a cell culture fermentation.

Yang et al. (1995; *Nucleic Acids Research* 23(11): 2041-2048) describe the expression of the full length TdT from chickens in *E. coli*. The recombinant TdT was cloned into the vector pET16b and was fused with a His tag to facilitate purification. Although analysis of the recombinant TdT after isolation resulted in a full length product, it had a 2-fold lower activity than native chicken TdT. In the opinion of the authors the reason for the lower activity of the recombinant TdT is either that the His tag interferes with the activity or it is due to the absence of a posttranslational modification.

Bouléet al. describe (1998, *Molecular Biotechnology* 10: 199-208) the expression of the full length TdT from the mouse in *E. coli*. The use of a strong promoter (T7 promoter) to increase the expression rate led at first to a high proportion of inactive expressed product (inclusion bodies). The authors subsequently avoided this by drastically decreasing the growth temperature during the induction phase (15° C.). However, a drawback of this is the retarded growth of the *E. coli* cells and the increased foam formation at these fermentation temperatures.

The object of the present invention was therefore to provide a TdT in a homogeneous form having an adequate enzymatic activity.

The object underlying the present invention is achieved by a truncated TdT enzyme from which 161 amino acids are missing at the N-terminus and which has an at least 20-fold increased enzymatic activity compared to the full length TdT from calf thymus. In particular those TdT enzymes have proven to be advantageous according to the invention which are shortened at the N-terminus by 100 to 160 amino acids. According to the invention a TdT which is shortened at the N-terminus by 138 amino acids is especially preferred. Such TdT derivatives have a 20- to 30-fold increased enzyme activity in solutions containing $Co^{2+}$ ions compared to the full length TdT from calf thymus. The truncated TdT according to the invention has a molecular weight (SDS-Page) of ca. 36 to 46 kDa, preferably between 40 and 46 kDa and in particular between 44 and 46 kDa.

Another subject matter of the invention is a method for the recombinant production of TdT from calf thymus which is characterized by the following steps:
a) transformation of a host cell with a nucleic acid which codes for an N-terminally truncated TdT fragment and is optionally fused with a nucleic acid which codes for a protein tag that facilitates the subsequent purification,
b) culture of the host cell to express the recombinant truncated TdT under suitable culture conditions for the respective host cell,
c) isolation of the recombinant truncated TdT from the host cell and
d) use and examination of the recombinant truncated TdT in a functional assay.

A host cell in the sense of the invention means any host cell which is able to actively express large amounts of proteins in the cytoplasm. These are usually prokaryotic cells such as *Escherichia coli* or *Bacillus subtilis*, but also yeast or fungal cells such as *Pichia pastoris, Pichia methylotropha, Hansenula polymorpha, Saccharomyces cerevisiae, Schizosaccharomaces pombae* among others or *Aspergillus* sp. have proven to be suitable. According to the invention *Escherichia coli* cells are preferably used.

In principle all fragments that can be derived from the cDNA of calf thymus TdT are potentially suitable as nucleic acids which code for an N-terminally truncated TdT fragment provided they code for a protein with TdT activity. In particular those nucleic acid sequences have proven to be advantageous according to the invention which code for a truncated TdT enzyme which lacks up to 161 amino acids at the N-terminus compared to the wild type enzyme. The following fragments have proven to be especially advantageous according to the invention: SEQ ID NO.: 7, SEQ ID NO.: 9 or SEQ ID NO.: 11.

The nucleic acid molecule coding for a truncated TdT protein can be fused with a nucleic acid sequence for the expression which codes for a protein that facilitates the subsequent purification of the expressed TdT. Suitable purification protein tags and the DNA fragments that encode them are in principle familiar to a person skilled in the art. In addition to the (poly)His tag, it is for example possible to use biotinylation proteins, streptavidin-binding proteins such as Streptacin® ("Inst. Für Bioanalytik, IBA", Göttingen/Germany), maltose-binding proteins (e.g. U.S. Pat. No. 5,643,758), GST and HA tags (e.g. U.S. Pat. No. 5,654,176; WO 98/17691) according to the invention.

Another subject matter of the invention is the purification of the truncated terminal transferase derivatives from the cytoplasm of the host cell. *E. coli* K12 UT5600 cells which overexpress the terminal transferase gene were used in particular as the starting material for the purification of the recombinant terminal transferase.

The TdT is usually purified at 4° C. After cell lysis and separation of the nucleic acids, which in principle can be carried out by known methods, a series of chromatographic steps are carried out. According to the invention the fraction freed from nucleic acids is firstly subjected to an ion-exchanger chromatography (cation exchanger) e.g. using a Poros HS 50 column. If a protein tag serving as a purification aid such as a (poly)His, a biotinylation peptide, Streptacin® or a maltose-binding protein is linked to the TdT derivative, i.e. has been co-expressed, an affinity chromatography is subsequently carried out. In the case of a TdT expression product linked to a (poly)His peptide, the commercially available nickel-chelate columns are especially suitable for this purification step. The resulting TdT fraction is subsequently further purified by a suitable hydrophobic chromatography for example on phenyl Sepharose fast flow (ff). The described purification method yields a very pure terminal transferase which is free from contaminating enzyme activities. The purity of Δ138-TdT having a molar mass of 45.3 kDa in an SDS gel is shown as an example in FIG. 1.

The truncated recombinant terminal transferase peptides according to the invention surprisingly have a substantially higher enzymatic activity in the activity test in solutions containing cobalt ($Co^{2+}$) ions (the so-called Co system) than native terminal transferase derivatives. The native terminal transferase exhibits a ca. three- to four-fold higher enzymatic activity in the Co system compared to the Zn/Mg system. In contrast the recombinant N-terminally truncated TdT derivatives exhibit a 20- to 30-fold increased activity. For example the Δ138-TdT derivative has a ca. 23-fold higher activity in the Co system than in the Zn/Mg system. Hence in contrast to native terminal transferase, the recombinant Δ138-TdT has a significantly higher enzyme activity in the Co system.

Figure 2:
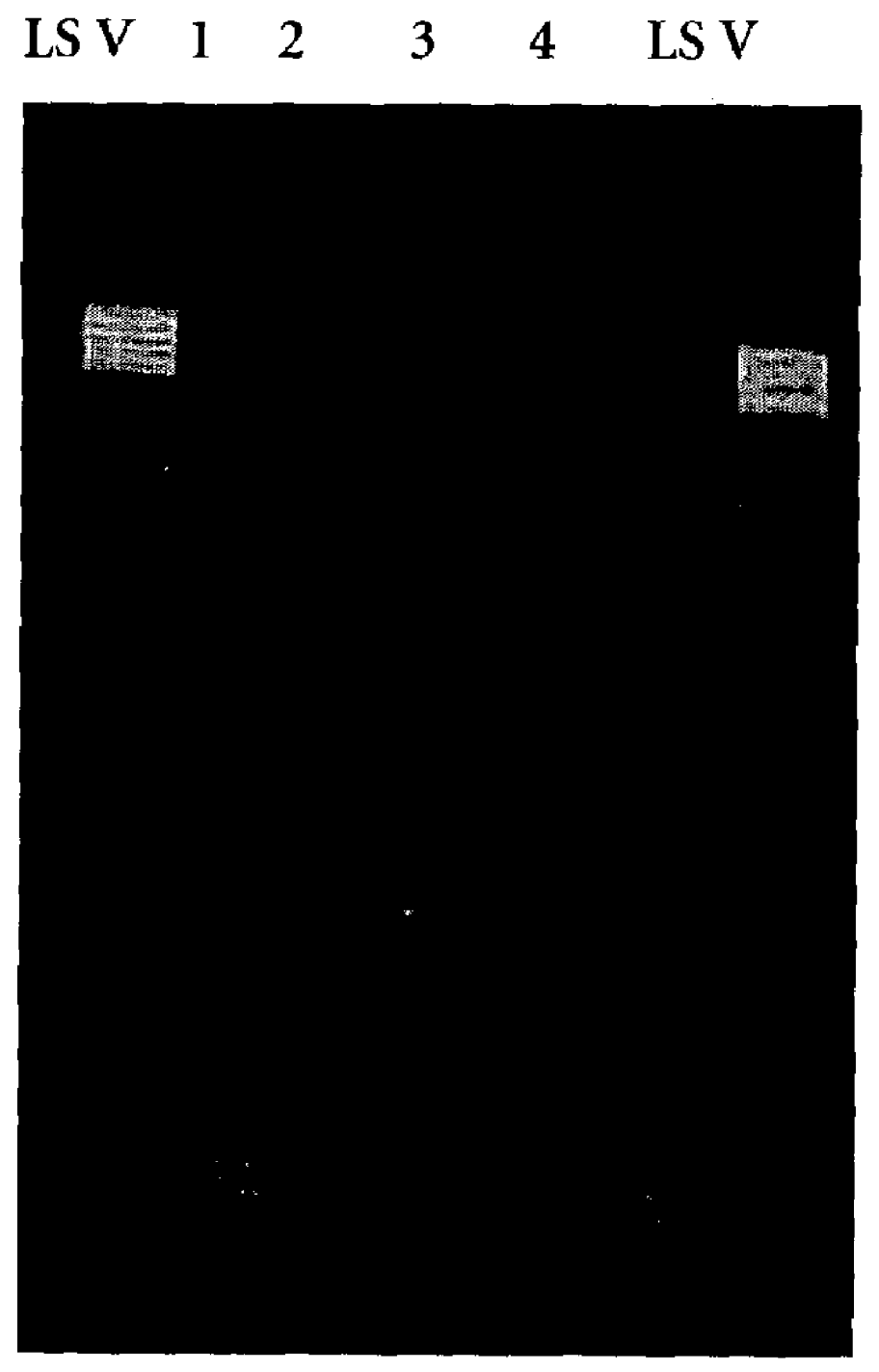

Moreover it is surprising that the recombinant Δ138-TdT derivative has a significantly better performance in the function test than the native terminal transferase. A 30mer oligonucleotide (5'-pTTG GGT AAC GCC AGG GTT TTC CCA GTC ACG OH-3') (SEQ ID NO: 13) was used as a template for the tailing reaction. After the reaction was completed, the reaction products of the tailing experiment were separated on a 6% agarose gel and evaluated (FIG. 2). The recombinant TdT resulted in a longer and hence better product of the tailing reaction.

FIGURE LEGENDS

FIG. 1: SDS gel electrophoresis of the purified terminal transferase (lane 1: molecular weight marker 12 (Novex Co.); lane 2: terminal transferase, 10 units (Zn/Mg system)

FIG. 2: Oligo tailing reaction (lanes 1, 4: oligonucleotide; lane 2: product of the tailing reaction, 10 units TdT, native; lane 3: product of the tailing reaction, 10 units TdT, recombinant; LSV: DNA molecular weight marker V (pBR 322 DNA cleaved with Hae III, 22 fragments 8-587 bp; Roche Diagnostics GmbH, Cat. No. 821 705))

LEGENDS FOR THE SEQUENCE PROTOCOLS

SEQ ID NO.:1 cDNA sequence of the TdT from calf thymus (pos. 22-1581)
SEQ ID NO.:2 amino acid sequence of the TdT from calf thymus (520 AA)
SEQ ID NO.:3 5' primer (58 N)
SEQ ID NO.:4 5' primer (63 N)
SEQ ID NO.:5 5' primer (60 N)
SEQ ID NO.:6 3' primer (42 N)
SEQ ID NO.:7 nucleic acid sequence coding for the truncated TdT, Δ138-TdT with His tag (1187 N)
SEQ ID NO.:8 amino acid sequence of the truncated TdT, Δ138-TdT with His tag (392 AA)
SEQ ID NO.:9 nucleic acid sequence coding for the truncated TdT, Δ151-TdT with His tag (1148 N)
SEQ ID NO.:10 amino acid sequence of the truncated TdT, Δ151-TdT with His tag (379 AA)
SEQ ID NO.:11 nucleic acid sequence coding for the truncated TdT, Δ160-TdT with His tag (1121 N)
SEQ ID NO.:12 amino acid sequence of the truncated TdT, Δ160-TdT with His tag (370 AA).
SEQ ID NO.:13 30mer oligonucleotide used as a template for the tailing reaction.
SEQ ID NO.:14 amino acid sequence of a His tag.
SEQ ID NO.:15 nucleic acid sequence coding for the truncated TdT, Δ152-TdT with His tag (1148 N)
SEQ ID NO.:16 amino acid sequence of the truncated TdT, Δ151-TdT with His tag (378 AA)
SEQ ID NO.:17 nucleic acid sequence coding for the truncated TdT, Δ161-TdT with His tag (1121 N)
SEQ ID NO.:18 amino acid sequence of the truncated TdT, Δ161-TdT with His tag (369 AA).

The invention is further elucidated by the following examples.

Recombinant DNA Technique

Standard methods were used to manipulate DNA as described by Sambrook, J. et al. (1989) Molecular cloning: A laboratory manual. Cold Spring Harbor Laboratory Press, Cold Spring Harbor, N.Y. The recommendations of the manufacturer were followed when using kits. The molecular biological reagents were used according to the instructions of the manufacturer.

EXAMPLE 1

Generation of Truncated TdT Genes

Oligonucleotides according to SEQ ID 3-6 which enable the isolation of truncated genes from the complete reading frame by means of PCR, were designed on the basis of a cDNA clone (Kowai et al. (1986), *Nucleic Acids Res.* 14: 5777-5792) having an insert of 1923 bp according to SEQ ID NO.:1 which contains the complete reading frame of the gene that codes for the terminal transferase according to SEQ ID NO.:2 from calf thymus. Each of the 5' primers (SEQ ID NO.: 3-5) were designed such that they contain the codons for the amino acids Met-Arg-Gly-Ser-His-His-His-His-His-His (SEQ ID NO: 14) downstream of the coding region and hence the truncated TdT peptides are N-terminally fused with a His tag. The 5' primers contain no recognition sequence for a restriction endonuclease, but should be cloned at the 5' end via a blunt end whereas the 3' primer has the recognition sequence for the restriction endonuclease HindIII downstream of the coding region.

In order to isolate a gene which codes for a TdT truncated by 138 amino acids at the N-terminus (Δ138-TdT), the PCR reaction was carried out using the oligonucleotides according to SEQ ID NO.: 3 (5' primer) and SEQ ID NO.: 6 (3' primer). The resulting PCR product according to SEQ ID NO.: 7 which codes for the Δ138-TdT with a His tag according to SEQ ID NO.: 8 was examined by sequencing.

In order to isolate a gene which codes for a TdT truncated by 152 amino acids at the N-terminus (Δ152-TdT), the PCR reaction was carried out using the oligo-nucleotides according to SEQ ID NO.: 4 (5' primer) and SEQ ID NO.: 6 (3' primer). The resulting PCR product according to SEQ ID NO.: 15 which codes for the Δ152-TdT with His tag according to SEQ ID NO.:16 was examined by sequencing.

In order to isolate a gene which codes for a TdT truncated by 161 amino acids at the N-terminus (Δ161-TdT), the PCR reaction was carried out using the oligo-nucleotides according to SEQ ID NO.: 5 (5' primer) and SEQ ID NO.: 6 (3' primer). The resulting PCR product according to SEQ ID NO.: 17 which codes for the Δ161-TdT with a His tag according to SEQ ID NO.: 18 was examined by sequencing.

Construction of the Expression Plasmids for the Truncated TdT Peptides

In order to express the TdT, the truncated genes were each cloned into expression vectors in such a manner that the structural genes were each inserted in the correct orientation under the control of a suitable promoter, preferably an IPTG-inducible promoter such as lac, lacUV5, tac or T5 promoter, particularly preferably the lac promoter. For this purpose the respective PCR product was recleaved at the 3' end with HindIII whereas the 5' end was not changed, the restriction mixtures were separated by agarose gel electrophoresis and the 1181 bp fragment was isolated from the agarose gel for the Δ138 TdT gene, the 1139 bp fragment was isolated for the Δ152 TdT gene and the 1115 bp fragment was isolated for the Δ161 TdT gene, each of which contained a nucleic acid which codes for the His tag. Various expression plasmids such as pUC, pDS, pQE, pKK but preferably pUC18 (Yanisch-Perron et al., (1985) Gene 33: 103-119) were used for the expression. In order to insert the genes for the truncated TdT peptides pUC18 was firstly cleaved with EcoRI (Roche Diagnostics) according to the manufacturer's instructions, the restriction endonuclease EcoRI was inactivated by incubating at 65° C. for 15 min and the resulting overhanging ends were filled in to form a blunt end using Klenow polymerase (Roche Diagnostics) according to the manufacturer's instructions. The Klenow polymerase was inactivated by incubating again at 65° C. for 15 min. Subsequently the vector fragment was cleaved with HindIII (Roche Diagnostics), the restriction mixture was separated by agarose gel electrophoresis and the resulting vector fragment of ca. 2656 bp was isolated from the agarose gel. The vector fragment obtained in this manner was separated and ligated with the isolated PCR products for the truncated TdT peptides. The correct insertion of the genes was checked by means of restriction control and sequencing.

The resulting plasmids pUC18Δ138-TdT, pUC18Δ152-TdT and pUC18Δ161-TdT (see FIG. 1) were cotransformed separately in various E. coli strains together with the helper plasmid pUBS520. The helper plasmid pUBS520 (Brinkmann et al., 1989, Gene 85: 109-114) carries among others the lacI$^q$-gene which codes for the lac repressor and the dnaY gene which codes for the rare tRNA$^{ARG}$ in E. coli (recognizes the codons AGA and AGG) (Garcia et al., 1986, Cell 45: 453-459). The kanamycin resistance gene from the transposon TN903 is used as the selection marker.

EXAMPLE 2

Transformation of the Expression Plasmids pUC18Δ38-TdT, pUC18Δ152-TdT and pUC18Δ161-TdT into Various E. coli Expression Strains Competent cells of various E. coli strains were produced according to the method of Hanahan (J. Mol. Biol. 1993, vol. 166: 557). 200 µl of cells prepared in this manner were admixed with 20 ng isolated expression plasmid DNA pUC18Δ138-TdT, pUC18Δ152-TdT and pUC18Δ161-TdT and 40 ng helper plasmid DNA. After 30 min incubation on ice, they were subjected to a heat shock (90 sec at 42° C.). Subsequently the cells were transferred to 1 ml LB medium and incubated for 1 hour at 37° C. in the LB medium for the phenotypic expression. Aliquots of this transformation mixture were plated out on LB plates containing ampicillin and kanamycin as selection markers and incubated for 15 hours at 37° C. Preferred strains are E. coli K12 C600, DH5α, LE392, JM83, JM105, NM522, M15, RR1Δ15, UT5600, TG1, A1200 or the strains E. coli B, BL21, HB101, Escherichia coli UT5600 is particularly preferred.

EXAMPLE 3

Expression of the Truncated TdT Genes in E. coli

In order to express the gene which codes for the truncated TdT peptides, plasmid-containing clones were inoculated in 3 ml LB$_{ampkan}$ medium and incubated at 37° C. in a shaker. The cells were induced with 0.5 mM IPTG at an optical density of 0.5 (measured at 550 nm, OD$_{550}$) and incubated for 4 h at 37° C. in a shaker. Subsequently the optical density of the individual expression clones was determined, an aliquot corresponding to an OD$_{550\,nm}$ of 5.0/ml was removed and the cells were centrifuged (10 min, 6000 rpm, 4° C.). The cell pellet was resuspended in 400 µl TE buffer (50 mM Tris/50 mM EDTA, pH 8.0), the cells were disrupted by ultrasound and the soluble protein fraction was separated from the insoluble protein fraction by centrifugation (10 min, 13800 rpm, 4° C.). Application buffer containing SDS and 2-mercapto-ethanol was added to all fractions and the proteins were denatured by boiling (5 min at 100° C.). Subsequently 10 µl aliquots were analysed by means of an analytical SDS gel (10%) (Laemmli U.K. 1970 Nature 227: 555-557).

The evaluation of the SDS gel showed that there is a clear overexpression of the truncated TdT fragments. An overexpressed additional band is observed at ca. 45 kDa (Δ138-TdT) or 44 kDa (Δ152-TdT) or 43 kDa (Δ161-TdT) which does not appear in the non-induced or induced but non-plasmid-containing control clones. All TdT fragments were detected in the soluble protein fraction when using this expression strategy even at high growth temperatures whereas corresponding bands at the same level were not detected in the insoluble protein fraction.

EXAMPLE 4

Determination of Terminal Transferase Activity

Various tests were carried out to determine terminal transferase activity.

1. Non-Radioactive Test (Test A)

The terminal transferase activity was detected in the fractions during purification by means of a non-radioactive test system. The DIG Oligo 3' end labeling Kit (Roche Diagnostics GmbH, Cat. No. 1 362 372) was used for this. The incubation time was extended to 30 minutes.

2. Radioactive Test Systems

A. Test in the Zn/Mg System (Test B)

The terminal transferase activity of the pools was determined by a radioactive test system which contained zinc and magnesium ions. The test for terminal transferase activity was carried out in a test volume of 60 µl (40 mM potassium cacodylate, pH 6.8, 0.33 mM $ZnSO_4$, 10 mM $MgCl_2$, 1 mM dATP, 0.1 AB poly $d(pT)_6$, 12.5 pM [3H]-dATP). Terminal transferase (10 µl) was added at suitable dilutions. After incubating for 30 min at 37° C., the reaction was stopped with 10% TCA solution (1000 µl). The radioactively-labelled product that formed was washed after precipitation on nitrocellulose filters. The rate of incorporation of radioactivity was measured in a scintilation counter and the terminal transferase activity of the sample was calculated. In this connection one enzyme unit was defined as the amount of terminal transferase which results in the incorporation of 1.0 nMol DAMP into acid-insoluble product within 60 min at 37° C.

This test is used to routinely determine the activity of native and recombinant terminal transferase.

B. Test in the Co System (Test C)

The terminal transferase activity was also determined using a test system which contained cobalt ions. This test was carried out in a test volume of 120 µl (200 mM potassium cacodylate, pH 7.2, 1 mM $CoCl_2$, 1 mM dTTP, 0.1 AB poly $d(pT)_6$, 37.5 pMol [3H]-dTTP). Terminal transferase (10 µl) was added at suitable dilutions. After incubating for 30 min at 37° C., the reaction was stopped with 10% TCA solution (1000 µl). The radioactively-labelled product that formed was washed after precipitation on nitrocellulose filters. The rate of incorporation of radioactivity was measured in a scintilation counter and the terminal transferase activity of the samples was calculated. In this connection one enzyme unit was defined as the amount of terminal transferase which results in the incorporation of 1.0 nMol dTMP or dATP into acid-insoluble product within 60 min at 37° C. using $d(pT)_6$ as a primer.

Test for Contaminating Activities

The test for the presence of contaminating foreign activities was carried out in a solution consisting of 10 mM Tris/HCl, pH 7.5, 10 mM $MgCl_2$, 1 mM DTE.

Suitable samples of the individual enzyme fractions were incubated with the corresponding nucleic acids. So-called nicking activity was detected by incubation with the plasmid pBR322 (1 µg) for 2-16 hours at 37° C. Unspecific nucleases were detected by incubation with lambda DNA/EcoRI, HindIII (1 µg) for 2-16 hours at 37° C.

For the test for contamination with exonucleases the samples were incubated for 4 hours at 37° C. with 4 µg [3H]-labelled DNA and afterwards the released [3H] -labelled nucleotides were determined.

EXAMPLE 5

Purification of Terminal Transferase

E. coli K12 UT5600 cells which overexpressed the terminal transferase gene (see above) were used as the starting material for purifying recombinant terminal transferase.

TdT was purified at 4° C. The purification was carried out after cell lysis and separation of the nucleic acids by a series of chromatographic steps. The purification process yields a recombinant TdT which is free from contaminating enzyme activities.

Solutions Used buffer A: 50 mM Tris/HCl, pH 7.6, 0.5 M NaCl, 50 mM LiCl
buffer B: 50 mM $KPO_4$, pH 6.0, 5% glycerol
buffer C: 50 mM Tris/HCl, pH 7.6, 0.5 M NaCl, 5% glycerol,
buffer D: 20 mM $KPO_4$, pH 7.0, 1.3 M ammonium sulfate, 5% glycerol
storage buffer: 60 mM $KPO_4$, pH 7.2, 150 mM KCl, 1 mM 2-mercaptoethanol, 0.5 % Triton X-100, 50% glycerol.

Cell Lysis

Ca. 1100 g cells of E. coli K12 UT5600 were admixed with 4000 ml buffer A, thawed and suspended. 20 ml 0.1 M PMSF solution (Roche Diagnostics GmbH, Cat. No. 236 608) was added to the suspension. The cells were subsequently lysed by means of high pressure dispersion (Gaulin Lab-60) while cooling (temperature: <10° C.). This resulted in a typical degree of lysis of the cell suspension of 40-50%.

Precipitation of Nucleic Acids

The nucleic acids were subsequently removed by means of Polymin precipitation. 100 ml of a 10% Polymin-P solution was added dropwise. In the case of an incomplete precipitation, an additional dropwise addition was carried out. The centrifugation (30 min, 5000 rpm, 4° C.) was carried out after incubation for 30 min at 4° C.

Chromatographic Purifications

Chromatography on Poros HS 50 Column

The dialysed centrifugation supernatant was applied to a Poros HS 50 column (9 cm×20 cm, PerSeptiv) equilibrated with buffer B+0.2 M NaCl and washed with ca. 10l buffer B+0.2 M NaCl. The enzyme was eluted with a linear gradient of buffer B+200 mM NaCl and buffer B+1 NaCl in a total volume of 8l. The flow rate was 100 ml per min, the fraction size was 100 ml. The terminal transferase elutes at an NaCl concentration of 300 mM to 700 mM.

Affinity Chromatography on Ni-chelate Column

The dear pool was adjusted to pH 7.5 with $K_2HPO_4$ and admixed with 1/100 buffer C+1 M imidazole and subsequently applied to a chelating Sepharose ff column (2.6 cm×10 cm, Pharmacia) equilibrated with buffer C+10 mM imidazole and loaded with nickel; it was afterwards washed with ca. 800 ml buffer C+20 mM imidazole, then washed with buffer C+30 mM imidazole. The enzyme was eluted with a linear gradient of buffer C+30 ml imidazole and buffer C+1 M imidazole in a total volume of 600 ml. The flow rate was 12 ml per minute and the fraction size was 25 ml per fraction. The enzyme eluted at a concentration of 50 mM to 200 mM imidazole.

All active fractions were pooled. Solid ammonium sulfate was added to the pool to a final concentration of 1.3 M.

Chromatography on Phenyl Sepharose ff

The pool was then applied to a phenyl Sepharose ff column (2.6 cm×10 cm, Pharmacia) equilibrated with buffer D. The column was firstly washed with ca. 400 ml buffer D and then with ca. 600 ml buffer D+500 mM ammonium sulfate. The enzyme was eluted in this washing step. The flow rate was 10 ml per min, the fraction size was 10 ml.

The active fractions were pooled and dialysed against storage buffer. In order to analyse the purity, application buffer containing SDS and 2-mercaptoethanol was added to the purified protein and the sample was denatured by boiling (5 min 100° C.). Subsequently a sample (20 µl) was analysed by means of an analytical SDS gel (4-20%) (Laemmli U.K. 1970 Nature 227: 555-557). The described purification method yields a highly pure terminal transferase having a molar mass of 45.3 kDa (FIG. 1).

EXAMPLE 6

Comparison of the Activities of Native and Recombinant Terminal Transferases

Due to the improved performance of the recombinant terminal transferase in the tailing reaction, the enzyme activities of the two terminal transferases were examined in two different test systems. The Zn/Mg system (test B) and the Co system (test C) were used for this.

TABLE 1

Activities of native and recombinant terminal transferase in different test systems (Zn/Mg system and Co system)

| | 1st Test (U/µl) | 2nd Test (U/µl) | 3rd Test (U/µl) | 4th Test (U/µl) | mean (U/µl) |
|---|---|---|---|---|---|
| a) Zn/Mg-system | | | | | |
| TdT, recombinant | 36.0 | 25.8 | 31.3 | 27.9 | 30.3 |
| TdT, native | 99.0 | 85.6 | 86.9 | 92.3 | 91 |
| b) Co system | | | | | |
| TdT recombinant | 841 | 668 | 676 | 705 | 722.5 |
| TdT, native | 452 | 436 | 273 | 312 | 368.3 |

The native terminal transferase has a ca. three to four-fold higher activity in the Co system than in the Zn/Mg system. In contrast the recombinant terminal transferase has a ca. 23-fold higher activity in the Co system than in the Zn/Mg system. In comparison to the native terminal transferase the recombinant terminal transferase thus has a more pronounced improvement of the enzyme activity in the Co system.

This difference in activity could be the explanation for the improved performance of the recombinant terminal transferase in the tailing reaction.

EXAMPLE 7

Function Test for Terminal Transferase

The recombinant terminal transferase that was obtained was examined in a function test. The function test consists of an oligo tailing reaction. For this 10 units of the recombinant TdT and the native TdT was used in a "Dig Oligonucleotide Tailing" kit (Cat. No. 1 417 231, Roche Diagnostics GmbH). 100 pmol of a 30mer oligonucleotide (5'-pTTG GGT AAC GCC AGG GTT TTC CCA GTC ACG OH-3') (SEQ ID NO: 13) was used as the template for the tailing reaction.

The reaction products of the tailing experiment were separated on a 6% agarose gel and evaluated (FIG. 2). The recombinant TdT resulted in a longer and hence better product of the tailing reaction.

Comparison of TdT According to the Invention with Known Preparations

TABLE 2

Activities of native and recombinant TdT and of TdT preparations of various manufacturers in different test systems.

| preparation/lot | source | Zn/Mg system [U/µl] | Co system [U/µl] |
|---|---|---|---|
| truncated TdT | E. coli, rec. (calf thymus) | 30.3 | 722.5 |
| TdT, native [55 U/µl] | calf thymus | 91.0 | 368.3 |
| TdT, native Stratagene Lot: 0610233 [28 U/µl] | calf thymus | 9.4 | 47.8 |
| TdT, native Amersham Pharmacia Lot: 5473 [15 U/µl] | calf thymus | 11.3 | 72.3 |
| TdT BRL Lot: 1093333 ]15 U/µl] | Baculovirus, rec. (calf thymus) | 2.7 | 20.4 |
| TdT, native Promega Lot: 91884 [20 U/µl] | calf thymus | 39.9 | 70.9 |
| TdT NEBL Lot: 2A [20 U/µl] | E. coli, rec. (calf thymus) | 24.7 | 42.4 |

Literature

Brinkmann U., Mattes R. E. und Buckel P. (1989), *Gene* 85: pp. 109-114

Boulé J. -B., Johnson E., Rougeon F. und Papanicolaou C. (1998), *Molecular Biotechnology* 10: pp. 199-208

Chang L. M., Plevani P. und Bollum F. J. (1982), *J. Biol. Chem.* 257(10): pp. 5700-5706

Chang L. M. und Bollum F. J. (1986), *CRC Crit Rev Biochem* 21(1): pp. 27-52

Chang L. M., Rafter E., Rusquet-Valerius, Peterson R. C., White S. T. und Bollum F. J. (1986), *J. Biol. Chem.* 263 (25): pp. 12509-12513

Deibel Jr. M. R. und Coleman M. S.(1979), *J. Biol. Chem.* 254(17): pp 8634-8640

Garcia G. M., Mar P. K., Mullin D. A., Walker J. R. und Prather N. E (1986), *Cell* 45: pp.453-459

Hanahan D. (1983), *J. Mol. Biol. Vol.* 166 pp. 557

Koiwai O., Yokota T., Kageyama T., Hirose T., Yoshida S. und Arai K. -I. (1986), *Nucleic Acid Research* 14 (14), pp. 5777-5792

Laemmli U. K. (1970), *Nature* 227: pp. 555-557

Peterson R. C., Cheung L. C., Mattaliano R. J., White S. T., Chang L. M. S. und Bollum F. J. (1985), *J Biol Chem* 260 (19):pp10495-502

Sambrook J., Fritsch E. F. und Maniatis T., (1989), In *Molecular cloning: A Laboratory Manual* second Edition Cold Spring Harbor Laboratory Press NY (USA)

Yang B., Gathy K. N. und Coleman M. S. (1995); *Nucleic Acids Research* 23 (11): pp. 2041-2048

U.S. Pat. No. 5,037,756 Inventors Bollum F. J., Chang L. M. S. und Peterson R. C.

We claim:

1. A recombinantly expressed terminal deoxynucleotidyl transferase (TdT) fusion protein comprising a truncated terminal deoxynucleotidyl transferase sequence and a protein tag sequence N-terminally fused to said truncated terminal deoxynucleotidyl transferase sequence, wherein said protein tag is selected from the group consisting of a His tag, Streptavidin binding proteins, Maltose binding proteins, GST and HA tags, and wherein the truncated terminal deoxynucleotidyl transferase sequence consists of the native calf thymus TdT sequence of SEQ ID NO: 2 N-terminally truncated by 138, 152, or 161 amino acids, wherein said recombinantly expressed terminal deoxynucleotidyl transferase fusion protein has a 20- to 30-fold higher enzyme activity in solutions containing Co2+ ions relative to solutions containing Zn/Mg ions.

2. A recombinantly expressed terminal deoxynucleotidyl transferase (TdT) fusion protein comprising a truncated terminal deoxynucleotidyl transferase sequence and a protein tag sequence N-terminally fused to said truncated terminal deoxynucleotidyl transferase sequence, wherein said protein tag is selected from the group consisting of a His tag, Streptavidin binding proteins, Maltose binding proteins, GST and HA tags, and wherein the truncated terminal deoxynucleotidyl transferase sequence consists of the native calf thymus TdT sequence of SEQ ID NO: 2 N-terminally truncated by 100 to 160 amino acids, wherein said recombinantly expressed terminal deoxynucleotidyl transferase fusion protein has a 20- to 30-fold higher enzyme activity in solutions containing Co2+ ions relative to solutions containing Zn/Mg ions.

3. The recombinantly expressed terminal deoxynucleotidyl transferase fusion protein of claim 1, wherein the truncated terminal deoxynucleotidyl transferase sequence is shortened at the N-terminus by 138 amino acids, has a molecular weight between 44 and 46 kDa (SDS page) and has a 20- to 25-fold increased enzyme activity in solutions containing Co2+ ions compared to native TdT.

4. A composition comprising a homogenous population of a recombinantly expressed terminal deoxynucleotidyl transferase (TdT) fusion protein, wherein the recombinantly expressed terminal deoxynucleotidyl transferase comprises a truncated terminal deoxynucleotidyl transferase sequence and a His tag sequence N-terminally fused to said truncated terminal deoxynucleotidyl transferase sequence, wherein said truncated terminal deoxynucleotidyl transferase sequence consists of the sequence of SEQ ID NO: 2 N-terminally truncated by at least 100 amino acids and up to 160 amino acids, wherein said recombinantly expressed terminal deoxynucleotidyl transferase fusion protein has a 20- to 30-fold higher enzyme activity in solutions containing Co2+ ions relative to solutions containing Zn/Mg ions.

5. The composition of claim 4 wherein the truncated terminal deoxynucleotidyl transferase sequence consists of the sequence of SEQ ID NO: 2N-terminally truncated by 138 amino acids.

6. The composition of claim 4 wherein the truncated terminal deoxynucleotidyl transferase sequence consists of the sequence of SEQ ID NO: 2 N-terminally truncated by 152 amino acids.

7. The recombinantly expressed terminal deoxynucleotidyl transferase fusion protein of claim 1 wherein the truncated terminal deoxynucleotidyl transferase sequence consists of the sequence of SEQ ID NO: 2 N-terminally truncated by 161 amino acids.

8. The recombinantly expressed terminal deoxynucleotidyl transferase fusion protein of claim 1 wherein said protein tag sequence is a (poly) histidine peptide.

9. The recombinantly expressed terminal deoxynucleotidyl transferase fusion protein of claim 8 wherein said His tag consists of the sequence Met-Arg-Gly-Ser-His-HiS-His-His-His-His (SEQ ID NO: 14).

10. The composition of claim 4 wherein the recombinantly expressed terminal deoxynucleotidyl transferase fusion protein consists of a polypeptide selected from the group consisting of SEQ ID NO: 8 and SEQ ID NO: 16.

11. The recombinantly expressed terminal deoxynucleotidyl transferase (TdT) fusion protein of claim 1, wherein the recombinantly expressed terminal deoxynucleotidyl transferase fusion protein consists of the polypeptide of SEQ ID NO: 18.

* * * * *

UNITED STATES PATENT AND TRADEMARK OFFICE
CERTIFICATE OF CORRECTION

| | |
|---|---|
| PATENT NO. | : 7,494,797 B2 |
| APPLICATION NO. | : 10/406136 |
| DATED | : February 24, 2009 |
| INVENTOR(S) | : Mueller et al. |

It is certified that error appears in the above-identified patent and that said Letters Patent is hereby corrected as shown below:

In claim 4, column 27, line 25, please delete "expressed terminal deoxynucleotidyl transferase comprises a" and insert -- expressed terminal deoxynucleotidyl transferase fusion protein comprises a -- therefor.

In claim 5, column 28, line 5, please insert a space between "NO:2" and "N-terminally.".

In claim 9, column 28, line 21, please delete "HiS" and insert -- His -- therefor.

Signed and Sealed this

Fourteenth Day of April, 2009

JOHN DOLL
*Acting Director of the United States Patent and Trademark Office*

SEQUENCE LISTING

<160> NUMBER OF SEQ ID NOS: 12

<210> SEQ ID NO 1
<211> LENGTH: 1923
<212> TYPE: DNA
<213> ORGANISM: Calf thymus

<400> SEQUENCE: 1

| | | | | | |
|---|---|---|---|---|---|
| ctcttctgga | gataccactt | gatggcacag | cagaggcagc | atcagcgtct | tcccatggat | 60 |
| ccgctgtgca | cagcctcctc | aggccctcgg | aagaagagac | ccaggcaggt | gggtgcctca | 120 |
| atggcctccc | ctcctcatga | catcaagttt | caaaatttgg | tcctcttcat | tttggagaag | 180 |
| aaaatgggaa | ccacccgcag | aaacttcctc | atggagctgg | ctcgaaggaa | aggtttcagg | 240 |
| gttgaaaatg | agctcagtga | ttctgtcacc | cacattgtag | cagaaaacaa | ctctggttca | 300 |
| gaggttctcg | agtggcttca | ggtacagaac | ataagagcca | gctcgcagct | agaactcctt | 360 |
| gatgtctcct | ggctgatcga | aagtatggga | gcaggaaaac | cagtggagat | tacaggaaaa | 420 |
| caccagcttg | ttgtgagaac | agactattca | gctaccccaa | acccaggctt | ccagaagact | 480 |
| ccaccacttg | ctgtaaaaaa | gatctcccag | tacgcgtgtc | aaagaaaaac | cactttgaac | 540 |
| aactataacc | acatattcac | ggatgccttt | gagatactgg | ctgaaaattc | tgagtttaaa | 600 |
| gaaaatgaag | tctcttatgt | gacatttatg | agagcagctt | ctgtacttaa | atctctgcca | 660 |
| ttcacaatca | tcagtatgaa | ggatacagaa | ggaattccct | gcctggggga | caaggtgaag | 720 |
| tgtatcatag | aggaaattat | tgaagatgga | gaaagttctg | aagttaaagc | tgtgttaaat | 780 |
| gatgaacgat | atcagtcctt | caaactcttt | acttctgttt | ttggagtggg | actgaagaca | 840 |
| tctgagaaat | ggttcaggat | ggggttcaga | tctctgagta | aaataatgtc | agacaaaacc | 900 |
| ctgaaattca | caaaaatgca | gaaagcagga | tttctctatt | atgaagacct | tgtcagctgc | 960 |
| gtgaccaggg | ccgaagcaga | ggcggttggc | gtgctggtta | aagaggctgt | gtgggcattt | 1020 |
| ctgccggatg | cctttgtcac | catgacagga | ggattccgca | ggggtaagaa | gattgggcat | 1080 |
| gatgtagatt | ttttaattac | cagcccagga | tcagcagagg | atgaagagca | acttttgcct | 1140 |
| aaagtgataa | acttatggga | aaaaagggga | ttactttat | attatgacct | tgtggagtca | 1200 |
| acatttgaaa | agttcaagtt | gccaagcagg | caggtggata | ctttagatca | ttttcaaaaa | 1260 |
| tgctttctga | ttttaaaatt | gcaccatcag | agagtagaca | gtagcaagtc | caaccagcag | 1320 |
| gaaggaaaga | cctggaaggc | catccgtgtg | gacctggtta | tgtgccccta | cgagaaccgt | 1380 |
| gcctttgccc | tgctaggctg | gactggctcc | cggcagtttg | agagagacat | ccggcgctat | 1440 |
| gccacacacg | agcggaagat | gatgctggat | aaccacgctt | tatatgacaa | gaccaagagg | 1500 |
| gtatttctca | aagcggaaag | tgaagaagaa | atctttgcac | atctgggatt | ggactacatt | 1560 |
| gaaccatggg | aaagaaatgc | ttaggagaaa | gctgtcaact | ttttctttt | ctgttctttt | 1620 |
| tttcaggtta | gacaaattat | gcttcatatt | ataatgaaag | atgccttagt | caagtttggg | 1680 |
| attctttaca | ttttaccaag | atgtagattg | cttctagaaa | taagtagttt | tggaaacgtg | 1740 |
| atcaggcacc | ccctgggtta | tgctctggca | agccatttgc | aggactgatg | tgtagaactc | 1800 |
| gcaatgcatt | ttccatagaa | acagtgttgg | aattggtggc | tcatttccag | ggaagttcat | 1860 |
| caaagcccac | tttgcccaca | gtgtagctga | aatactgtat | acttgccaat | aaaaatagga | 1920 |
| aac | | | | | 1923 |

<210> SEQ ID NO 2
<211> LENGTH: 520
<212> TYPE: PRT
<213> ORGANISM: Calf thymus

<400> SEQUENCE: 2

| Met | Ala | Gln | Gln | Arg | Gln | His | Gln | Arg | Leu | Pro | Met | Asp | Pro | Leu | Cys |
|---|---|---|---|---|---|---|---|---|---|---|---|---|---|---|---|
| 1 | | | | 5 | | | | | 10 | | | | | 15 | |

| Thr | Ala | Ser | Ser | Gly | Pro | Arg | Lys | Lys | Arg | Pro | Arg | Gln | Val | Gly | Ala |
|---|---|---|---|---|---|---|---|---|---|---|---|---|---|---|---|
| | | | 20 | | | | | 25 | | | | | 30 | | |

| Ser | Met | Ala | Ser | Pro | Pro | His | Asp | Ile | Lys | Phe | Gln | Asn | Leu | Val | Leu |
|---|---|---|---|---|---|---|---|---|---|---|---|---|---|---|---|
| | | | 35 | | | | | 40 | | | | | 45 | | |

| Phe | Ile | Leu | Glu | Lys | Lys | Met | Gly | Thr | Thr | Arg | Arg | Asn | Phe | Leu | Met |
|---|---|---|---|---|---|---|---|---|---|---|---|---|---|---|---|
| 50 | | | | | 55 | | | | | 60 | | | | | |

| Glu | Leu | Ala | Arg | Arg | Lys | Gly | Phe | Arg | Val | Glu | Asn | Glu | Leu | Ser | Asp |
|---|---|---|---|---|---|---|---|---|---|---|---|---|---|---|---|
| 65 | | | | | 70 | | | | | 75 | | | | | 80 |

| Ser | Val | Thr | His | Ile | Val | Ala | Glu | Asn | Asn | Ser | Gly | Ser | Glu | Val | Leu |
|---|---|---|---|---|---|---|---|---|---|---|---|---|---|---|---|
| | | | | 85 | | | | | 90 | | | | | 95 | |

| Glu | Trp | Leu | Gln | Val | Gln | Asn | Ile | Arg | Ala | Ser | Ser | Gln | Leu | Glu | Leu |
|---|---|---|---|---|---|---|---|---|---|---|---|---|---|---|---|
| | | | | 100 | | | | | 105 | | | | | 110 | |

| Leu | Asp | Val | Ser | Trp | Leu | Ile | Glu | Ser | Met | Gly | Ala | Gly | Lys | Pro | Val |
|---|---|---|---|---|---|---|---|---|---|---|---|---|---|---|---|
| | | | 115 | | | | | 120 | | | | | 125 | | |

| Glu | Ile | Thr | Gly | Lys | His | Gln | Leu | Val | Val | Arg | Thr | Asp | Tyr | Ser | Ala |
|---|---|---|---|---|---|---|---|---|---|---|---|---|---|---|---|
| | | | 130 | | | | | 135 | | | | | 140 | | |

| Thr | Pro | Asn | Pro | Gly | Phe | Gln | Lys | Thr | Pro | Pro | Leu | Ala | Val | Lys | Lys |
|---|---|---|---|---|---|---|---|---|---|---|---|---|---|---|---|
| 145 | | | | | 150 | | | | | 155 | | | | | 160 |

| Ile | Ser | Gln | Tyr | Ala | Cys | Gln | Arg | Lys | Thr | Thr | Leu | Asn | Asn | Tyr | Asn |
|---|---|---|---|---|---|---|---|---|---|---|---|---|---|---|---|
| | | | | 165 | | | | | 170 | | | | | 175 | |

| His | Ile | Asp | Ala | Phe | Glu | Ile | Leu | Ala | Glu | Asn | Ser | Glu | Phe | Lys | Glu |
|---|---|---|---|---|---|---|---|---|---|---|---|---|---|---|---|
| | | | 180 | | | | | 185 | | | | | 190 | | |

| Asn | Glu | Val | Ser | Tyr | Val | Thr | Phe | Met | Arg | Ala | Ala | Ser | Val | Leu | Lys |
|---|---|---|---|---|---|---|---|---|---|---|---|---|---|---|---|
| | | | 195 | | | | | 200 | | | | | 205 | | |

| Ser | Leu | Pro | Phe | Thr | Ile | Ile | Ser | Met | Lys | Asp | Thr | Phe | Thr | Glu | Gly |
|---|---|---|---|---|---|---|---|---|---|---|---|---|---|---|---|
| | 210 | | | | | 215 | | | | | 220 | | | | |

| Ile | Pro | Cys | Leu | Gly | Asp | Lys | Val | Lys | Cys | Ile | Ile | Glu | Glu | Ile | Ile |
|---|---|---|---|---|---|---|---|---|---|---|---|---|---|---|---|
| 225 | | | | | 230 | | | | | 235 | | | | | 240 |

| Glu | Asp | Gly | Glu | Ser | Ser | Glu | Val | Lys | Ala | Val | Leu | Asn | Asp | Glu | Arg |
|---|---|---|---|---|---|---|---|---|---|---|---|---|---|---|---|
| | | | | 245 | | | | | 250 | | | | | 255 | |

| Tyr | Gln | Ser | Phe | Lys | Leu | Ser | Val | Phe | Gly | Val | Gly | Leu | Lys | Thr | Ser |
|---|---|---|---|---|---|---|---|---|---|---|---|---|---|---|---|
| | | | 260 | | | | | 265 | | | | | 270 | | |

| Glu | Lys | Trp | Phe | Arg | Met | Gly | Phe | Thr | Phe | Arg | Ser | Leu | Ser | Lys | Ile |
|---|---|---|---|---|---|---|---|---|---|---|---|---|---|---|---|
| | 275 | | | | | 280 | | | | | 285 | | | | |

| Met | Ser | Asp | Lys | Thr | Leu | Lys | Lys | Met | Gln | Lys | Ala | Gly | Phe | Leu | Tyr |
|---|---|---|---|---|---|---|---|---|---|---|---|---|---|---|---|
| | 290 | | | | | 295 | | | | | 300 | | | | |

| Tyr | Glu | Asp | Leu | Val | Ser | Cys | Val | Thr | Arg | Ala | Glu | Ala | Glu | Ala | Val |
|---|---|---|---|---|---|---|---|---|---|---|---|---|---|---|---|
| 305 | | | | | 310 | | | | | 315 | | | | | 320 |

| Gly | Val | Leu | Val | Lys | Glu | Ala | Val | Trp | Ala | Phe | Leu | Pro | Asp | Ala | Phe |
|---|---|---|---|---|---|---|---|---|---|---|---|---|---|---|---|
| | | | | 325 | | | | | 330 | | | | | 335 | |

| Val | Thr | Met | Thr | Gly | Gly | Phe | Arg | Arg | Gly | Lys | Lys | Ile | Gly | His | Asp |
|---|---|---|---|---|---|---|---|---|---|---|---|---|---|---|---|
| | | | 340 | | | | | 345 | | | | | 350 | | |

| Val | Asp | Phe | Leu | Ile | Thr | Ser | Pro | Gly | Ser | Ala | Glu | Asp | Glu | Glu | Gln |
|---|---|---|---|---|---|---|---|---|---|---|---|---|---|---|---|
| | | | 355 | | | | | 360 | | | | | 365 | | |

| Leu | Leu | Pro | Lys | Val | Ile | Asn | Leu | Trp | Glu | Lys | Lys | Gly | Leu | Leu | Leu |
|---|---|---|---|---|---|---|---|---|---|---|---|---|---|---|---|
| | 370 | | | | | 375 | | | | | 380 | | | | |

Tyr Tyr Asp Leu Val Glu Ser Thr Phe Glu Lys Phe Lys Phe Thr Leu
385                 390                 395                 400

Pro Ser Arg Gln Val Asp Thr Leu Asp His Phe Gln Lys Cys Phe Leu
        405                 410                 415

Ile Leu Lys Leu His His Gln Arg Val Asp Ser Ser Lys Ser Asn Gln
            420                 425                 430

Gln Glu Gly Lys Thr Trp Lys Ala Ile Arg Val Asp Leu Val Met Cys
        435                 440                 445

Pro Tyr Glu Asn Arg Ala Phe Ala Leu Leu Gly Trp Thr Gly Ser Arg
    450                 455                 460

Gln Phe Glu Arg Asp Ile Arg Arg Tyr Ala Thr His Glu Arg Lys Met
465                 470                 475                 480

Met Leu Asp Asn His Ala Leu Tyr Asp Lys Thr Lys Arg Val Phe Leu
            485                 490                 495

Lys Ala Glu Ser Glu Glu Glu Ile Phe Ala His Leu Gly Leu Asp Tyr
        500                 505                 510

Ile Glu Pro Trp Glu Arg Asn Ala
    515                 520

<210> SEQ ID NO 3
<211> LENGTH: 58
<212> TYPE: DNA
<213> ORGANISM: Artificial Sequence
<220> FEATURE:
<223> OTHER INFORMATION: Primer sequence

<400> SEQUENCE: 3
atgagaggat cgcatcacca tcaccatcac agaacagact attcagctac cccaaacc       58

<210> SEQ ID NO 4
<211> LENGTH: 63
<212> TYPE: DNA
<213> ORGANISM: Artificial Sequence
<220> FEATURE:
<223> OTHER INFORMATION: Primer sequence

<400> SEQUENCE: 4
atgagaggat cgcatcacca tcaccatcac aagactccac cacttgctgt aaaaaagatc     60
tcc                                                                    63

<210> SEQ ID NO 5
<211> LENGTH: 60
<212> TYPE: DNA
<213> ORGANISM: Artificial Sequence
<220> FEATURE:
<223> OTHER INFORMATION: Primer sequence

<400> SEQUENCE: 5
atgagaggat cgcatcacca tcaccatcac atctcccagt acgcgtgtca agaaaaacc      60

<210> SEQ ID NO 6
<211> LENGTH: 42
<212> TYPE: DNA
<213> ORGANISM: Artificial Sequence
<220> FEATURE:
<223> OTHER INFORMATION: Primer sequence

<400> SEQUENCE: 6
gcgcaagctt aagcatttct ttcccatggt tcaatgtagt cc                         42

<210> SEQ ID NO 7

<211> LENGTH: 1187
<212> TYPE: DNA
<213> ORGANISM: Calf thymus

<400> SEQUENCE: 7

| | | | | | |
|---|---|---|---|---|---|
| atgagaggat | cgcatcacca | tcaccatcac | agaacagact | attcagctac | cccaaaccca | 60 |
| ggcttccaga | agactccacc | acttgctgta | aaaaagatct | cccagtacgc | gtgtcaaaga | 120 |
| aaaaccactt | tgaacaacta | taaccacata | ttcacggatg | cctttgagat | actggctgaa | 180 |
| aattctgagt | ttaaagaaaa | tgaagtctct | tatgtgacat | ttatgagagc | agcttctgta | 240 |
| cttaaatctc | tgccattcac | aatcatcagt | atgaaggata | cagaaggaat | tccctgcctg | 300 |
| ggggacaagg | tgaagtgtat | catagaggaa | attattgaag | atggagaaag | ttctgaagtt | 360 |
| aaagctgtgt | taaatgatga | acgatatcag | tccttcaaac | tctttacttc | tgtttttgga | 420 |
| gtgggactga | agacatctga | gaaatggttc | aggatggggt | tcagatctct | gagtaaaata | 480 |
| atgtcagaca | aaaccctgaa | attcacaaaa | atgcagaaag | caggatttct | ctattatgaa | 540 |
| gaccttgtca | gctgcgtgac | cagggccgaa | gcagaggcgg | ttgcgtgct | ggttaaagag | 600 |
| gctgtgtggg | catttctgcc | ggatgccttt | gtcaccatga | caggaggatt | ccgcaggggt | 660 |
| aagaagattg | gcatgatgt | agattttta | attaccagcc | caggatcagc | agaggatgaa | 720 |
| gagcaacttt | tgcctaaagt | gataaactta | tgggaaaaaa | agggattact | tttatattat | 780 |
| gaccttgtgg | agtcaacatt | tgaaaagttc | aagttgccaa | gcaggcaggt | ggatacttta | 840 |
| gatcattttc | aaaaatgctt | tctgatttta | aaattgcacc | atcagagagt | agacagtagc | 900 |
| aagtccaacc | agcaggaagg | aaagacctgg | aaggccatcc | gtgtggacct | ggttatgtgc | 960 |
| ccctacgaga | accgtgcctt | tgccctgcta | ggctggactg | gctcccggca | gtttgagaga | 1020 |
| gacatccggc | gctatgccac | acgagcgg | aagatgatgc | tggataacca | cgctttatat | 1080 |
| gacaagacca | agagggtatt | tctcaaagcg | gaaagtgaag | aagaaatctt | tgcacatctg | 1140 |
| ggattggact | acattgaacc | atgggaaaga | aatgcttaag | cttgcgc | | 1187 |

<210> SEQ ID NO 8
<211> LENGTH: 392
<212> TYPE: PRT
<213> ORGANISM: Calf thymus

<400> SEQUENCE: 8

Met Arg Gly Ser His His His His His His Arg Thr Asp Tyr Ser Ala
1               5                   10                  15

Thr Pro Asn Pro Gly Phe Gln Lys Thr Pro Leu Ala Val Lys Lys
            20                  25                  30

Ile Ser Gln Tyr Ala Cys Gln Arg Lys Thr Thr Leu Asn Asn Tyr Asn
        35                  40                  45

His Ile Asp Ala Phe Glu Ile Leu Ala Glu Asn Ser Glu Phe Lys Glu
    50                  55                  60

Asn Glu Val Ser Tyr Val Thr Phe Met Arg Ala Ala Ser Val Leu Lys
65                  70                  75                  80

Ser Leu Pro Phe Thr Ile Ile Ser Met Lys Asp Thr Phe Thr Glu Gly
                85                  90                  95

Ile Pro Cys Leu Gly Asp Lys Val Lys Cys Ile Ile Glu Glu Ile Ile
            100                 105                 110

Glu Asp Gly Glu Ser Ser Glu Val Lys Ala Val Leu Asn Asp Glu Arg
        115                 120                 125

Tyr Gln Ser Phe Lys Leu Ser Val Phe Gly Val Gly Leu Lys Thr Ser

|   |   |   | 130 |   |   |   | 135 |   |   |   | 140 |   |
|---|---|---|---|---|---|---|---|---|---|---|---|---|

Glu Lys Trp Phe Arg Met Gly Phe Thr Phe Arg Ser Leu Ser Lys Ile
145                 150                 155                 160

Met Ser Asp Lys Thr Leu Lys Lys Met Gln Lys Ala Gly Phe Leu Tyr
                165                 170                 175

Tyr Glu Asp Leu Val Ser Cys Val Thr Arg Ala Glu Ala Glu Ala Val
            180                 185                 190

Gly Val Leu Val Lys Glu Ala Val Trp Ala Phe Leu Pro Asp Ala Phe
        195                 200                 205

Val Thr Met Thr Gly Gly Phe Arg Arg Gly Lys Lys Ile Gly His Asp
210                 215                 220

Val Asp Phe Leu Ile Thr Ser Pro Gly Ser Ala Glu Asp Glu Glu Gln
225                 230                 235                 240

Leu Leu Pro Lys Val Ile Asn Leu Trp Glu Lys Lys Gly Leu Leu Leu
                245                 250                 255

Tyr Tyr Asp Leu Val Glu Ser Thr Phe Glu Lys Phe Lys Phe Thr Leu
            260                 265                 270

Pro Ser Arg Gln Val Asp Thr Leu Asp His Phe Gln Lys Cys Phe Leu
        275                 280                 285

Ile Leu Lys Leu His His Gln Arg Val Asp Ser Ser Lys Ser Asn Gln
290                 295                 300

Gln Glu Gly Lys Thr Trp Lys Ala Ile Arg Val Asp Leu Val Met Cys
305                 310                 315                 320

Pro Tyr Glu Asn Arg Ala Phe Ala Leu Leu Gly Trp Thr Gly Ser Arg
                325                 330                 335

Gln Phe Glu Arg Asp Ile Arg Arg Tyr Ala Thr His Glu Arg Lys Met
            340                 345                 350

Met Leu Asp Asn His Ala Leu Tyr Asp Lys Thr Lys Arg Val Phe Leu
        355                 360                 365

Lys Ala Glu Ser Glu Glu Ile Phe Ala His Leu Gly Leu Asp Tyr
370                 375                 380

Ile Glu Pro Trp Glu Arg Asn Ala
385                 390

<210> SEQ ID NO 9
<211> LENGTH: 1148
<212> TYPE: DNA
<213> ORGANISM: Calf thymus

<400> SEQUENCE: 9

| atgagaggat cgcatcacca tcaccatcac aagactccac cacttgctgt aaaaaagatc | 60 |
| tcccagtacg cgtgtcaaag aaaaaccact ttgaacaact ataaccacat attcacggat | 120 |
| gcctttgaga tactggctga aaattctgag tttaaagaaa atgaagtctc ttatgtgaca | 180 |
| tttatgagag cagcttctgt acttaaatct ctgccattca caatcatcag tatgaaggat | 240 |
| acagaaggaa ttccctgcct gggggacaag gtgaagtgta tcatagagga aattattgaa | 300 |
| gatggagaaa gttctgaagt taaagctgtg ttaaatgatg aacgatatca gtccttcaaa | 360 |
| ctctttactt ctgttttttgg agtgggactg aagacatctg agaaatggtt caggatgggg | 420 |
| ttcagatctc tgagtaaaat aatgtcagac aaaaccctga attcacaaa atgcagaaa | 480 |
| gcaggatttc tctattatga agaccttgtc agctgcgtga ccagggccga agcagaggcg | 540 |
| gttggcgtgc tggttaaaga ggctgtgtgg gcatttctgc cggatgcctt tgtcaccatg | 600 |
| acaggaggat tccgcagggg taagaagatt gggcatgatg tagattttt aattaccagc | 660 |

-continued

```
ccaggatcag cagaggatga agagcaactt ttgcctaaag tgataaactt atgggaaaaa    720
aagggattac ttttatatta tgaccttgtg gagtcaacat ttgaaaagtt caagttgcca    780
agcaggcagg tggatacttt agatcatttt caaaaatgct ttctgatttt aaaattgcac    840
catcagagag tagacagtag caagtccaac cagcaggaag aaagacctg aaggccatc     900 cgtgtggacc tggttatgtg cccctacgag aaccgtgcct ttgccctgct aggctggact    960
ggctcccggc agtttgagag agacatccgg cgctatgcca cacacgagcg aagatgatg   1020 ctggataacc acgctttata tgacaagacc aagagggtat ttctcaaagc ggaaagtgaa   1080
gaagaaatct ttgcacatct gggattggac tacattgaac catgggaaag aaatgcttaa   1140
gcttgcgc                                                           1148
```

<210> SEQ ID NO 10
<211> LENGTH: 379
<212> TYPE: PRT
<213> ORGANISM: Calf thymus

<400> SEQUENCE: 10

```
Met Arg Gly Ser His His His His His Lys Thr Pro Leu Ala
 1               5                  10                  15

Val Lys Lys Ile Ser Gln Tyr Ala Cys Gln Arg Lys Thr Thr Leu Asn
             20                  25                  30

Asn Tyr Asn His Ile Asp Ala Phe Glu Ile Leu Ala Glu Asn Ser Glu
         35                  40                  45

Phe Lys Glu Asn Glu Val Ser Tyr Val Thr Phe Met Arg Ala Ala Ser
     50                  55                  60

Val Leu Lys Ser Leu Pro Phe Thr Ile Ile Ser Met Lys Asp Thr Phe
 65                  70                  75                  80

Thr Glu Gly Ile Pro Cys Leu Gly Asp Lys Val Lys Cys Ile Ile Glu
                 85                  90                  95

Glu Ile Ile Glu Asp Gly Glu Ser Ser Glu Val Lys Ala Val Leu Asn
            100                 105                 110

Asp Glu Arg Tyr Gln Ser Phe Lys Leu Ser Val Phe Gly Val Gly Leu
        115                 120                 125

Lys Thr Ser Glu Lys Trp Phe Arg Met Gly Phe Thr Phe Arg Ser Leu
    130                 135                 140

Ser Lys Ile Met Ser Asp Lys Thr Leu Lys Lys Met Gln Lys Ala Gly
145                 150                 155                 160

Phe Leu Tyr Tyr Glu Asp Leu Val Ser Cys Val Thr Arg Ala Glu Ala
                165                 170                 175

Glu Ala Val Gly Val Leu Val Lys Glu Ala Val Trp Ala Phe Leu Pro
            180                 185                 190

Asp Ala Phe Val Thr Met Thr Gly Gly Phe Arg Arg Gly Lys Lys Ile
        195                 200                 205

Gly His Asp Val Asp Phe Leu Ile Thr Ser Pro Gly Ser Ala Glu Asp
    210                 215                 220

Glu Glu Gln Leu Leu Pro Lys Val Ile Asn Leu Trp Glu Lys Lys Gly
225                 230                 235                 240

Leu Leu Leu Tyr Tyr Asp Leu Val Glu Ser Thr Phe Glu Lys Phe Lys
                245                 250                 255

Phe Thr Leu Pro Ser Arg Gln Val Asp Thr Leu Asp His Phe Gln Lys
            260                 265                 270

Cys Phe Leu Ile Leu Lys Leu His His Gln Arg Val Asp Ser Ser Lys
```

```
                   275                 280                 285
Ser Asn Gln Gln Glu Gly Lys Thr Trp Lys Ala Ile Arg Val Asp Leu
    290                 295                 300

Val Met Cys Pro Tyr Glu Asn Arg Ala Phe Ala Leu Leu Gly Trp Thr
305                 310                 315                 320

Gly Ser Arg Gln Phe Glu Arg Asp Ile Arg Arg Tyr Ala Thr His Glu
                325                 330                 335

Arg Lys Met Met Leu Asp Asn His Ala Leu Tyr Asp Lys Thr Lys Arg
                340                 345                 350

Val Phe Leu Lys Ala Glu Ser Glu Glu Ile Phe Ala His Leu Gly
                355                 360                 365

Leu Asp Tyr Ile Glu Pro Trp Glu Arg Asn Ala
    370                 375

<210> SEQ ID NO 11
<211> LENGTH: 1121
<212> TYPE: DNA
<213> ORGANISM: Calf thymus

<400> SEQUENCE: 11
atgagaggat cgcatcacca tcaccatcac atctcccagt acgcgtgtca agaaaaaacc      60
actttgaaca actataacca catattcacg gatgcctttg agatactggc tgaaaattct     120
gagtttaaag aaaatgaagt ctcttatgtg acatttatga gagcagcttc tgtacttaaa     180
tctctgccat tcacaatcat cagtatgaag gatacagaag gaattccctg cctgggggac     240
aaggtgaagt gtatcataga ggaaattatt gaagatggag aaagttctga agttaaagct     300
gtgttaaatg atgaacgata tcagtccttc aaactcttta cttctgtttt tggagtggga     360
ctgaagacat ctgagaaatg gttcaggatg gggttcagat ctctgagtaa ataatgtca     420 gacaaaaccc tgaaattcac aaaaatgcag aaagcaggat ttctctatta tgaagacctt     480
gtcagctgcg tgaccagggc cgaagcagag gcggttggcg tgctggttaa agaggctgtg     540
tgggcatttc tgccggatgc ctttgtcacc atgacaggag gattccgcag gggtaagaag     600
attgggcatg atgtagattt tttaattacc agcccaggat cagcagagga tgaagagcaa     660
cttttgccta agtgataaa cttatgggaa aaaagggat tacttttata ttatgacctt     720
gtggagtcaa catttgaaaa gttcaagttg ccaagcaggc aggtggatac tttagatcat     780
tttcaaaaat gctttctgat tttaaaattg caccatcaga gagtagacag tagcaagtcc     840
aaccagcagg aaggaaagac ctggaaggcc atccgtgtgg acctggttat gtgcccctac     900
gagaaccgtg cctttgccct gctaggctgg actggctccc ggcagtttga gagagacatc     960
cggcgctatg ccacacacga gcggaagatg atgctggata ccacgcttt atatgacaag    1020 accaagaggg tatttctcaa agcggaaagt gaagaagaaa tctttgcaca tctgggattg    1080
gactacattg aaccatggga agaaatgct taagcttgcg c                         1121

<210> SEQ ID NO 12
<211> LENGTH: 370
<212> TYPE: PRT
<213> ORGANISM: Calf thymus

<400> SEQUENCE: 12

Met Arg Gly Ser His His His His His His Ile Ser Gln Tyr Ala Cys
1               5                   10                  15

Gln Arg Lys Thr Thr Leu Asn Asn Tyr Asn His Ile Asp Ala Phe Glu
                20                  25                  30
```

-continued

```
Ile Leu Ala Glu Asn Ser Glu Phe Lys Glu Asn Glu Val Ser Tyr Val
        35                  40                  45
Thr Phe Met Arg Ala Ala Ser Val Leu Lys Ser Leu Pro Phe Thr Ile
        50                  55                  60
Ile Ser Met Lys Asp Thr Phe Thr Glu Gly Ile Pro Cys Leu Gly Asp
65                  70                  75                  80
Lys Val Lys Cys Ile Ile Glu Glu Ile Ile Glu Asp Gly Glu Ser Ser
                85                  90                  95
Glu Val Lys Ala Val Leu Asn Asp Glu Arg Tyr Gln Ser Phe Lys Leu
            100                 105                 110
Ser Val Phe Gly Val Gly Leu Lys Thr Ser Glu Lys Trp Phe Arg Met
            115                 120                 125
Gly Phe Thr Phe Arg Ser Leu Ser Lys Ile Met Ser Asp Lys Thr Leu
        130                 135                 140
Lys Lys Met Gln Lys Ala Gly Phe Leu Tyr Tyr Glu Asp Leu Val Ser
145                 150                 155                 160
Cys Val Thr Arg Ala Glu Ala Glu Ala Val Gly Val Leu Val Lys Glu
                165                 170                 175
Ala Val Trp Ala Phe Leu Pro Asp Ala Phe Val Thr Met Thr Gly Gly
            180                 185                 190
Phe Arg Arg Gly Lys Lys Ile Gly His Asp Val Asp Phe Leu Ile Thr
        195                 200                 205
Ser Pro Gly Ser Ala Glu Asp Glu Glu Gln Leu Leu Pro Lys Val Ile
        210                 215                 220
Asn Leu Trp Glu Lys Lys Gly Leu Leu Leu Tyr Tyr Asp Leu Val Glu
225                 230                 235                 240
Ser Thr Phe Glu Lys Phe Lys Phe Thr Leu Pro Ser Arg Gln Val Asp
                245                 250                 255
Thr Leu Asp His Phe Gln Lys Cys Phe Leu Ile Leu Lys Leu His His
            260                 265                 270
Gln Arg Val Asp Ser Ser Lys Ser Asn Gln Gln Glu Gly Lys Thr Trp
        275                 280                 285
Lys Ala Ile Arg Val Asp Leu Val Met Cys Pro Tyr Glu Asn Arg Ala
        290                 295                 300
Phe Ala Leu Leu Gly Trp Thr Gly Ser Arg Gln Phe Glu Arg Asp Ile
305                 310                 315                 320
Arg Arg Tyr Ala Thr His Glu Arg Lys Met Met Leu Asp Asn His Ala
                325                 330                 335
Leu Tyr Asp Lys Thr Lys Arg Val Phe Leu Lys Ala Glu Ser Glu Glu
            340                 345                 350
Glu Ile Phe Ala His Leu Gly Leu Asp Tyr Ile Glu Pro Trp Glu Arg
            355                 360                 365
Asn Ala
    370
```